US010820997B2

(12) United States Patent
Nathe et al.

(10) Patent No.: US 10,820,997 B2
(45) Date of Patent: Nov. 3, 2020

(54) HEART IMPLANT

(71) Applicant: coramaze technologies GmbH, Hilden (DE)

(72) Inventors: Niklas Maximilian Nathe, Düsseldorf (DE); Raz Bar-On, Hadera (IL); Stefan Daniel Menzl, Jona (CH)

(73) Assignee: coramaze technologies GmbH, Hilden (DE)

(*) Notice: Subject to any disclaimer, the term of this patent is extended or adjusted under 35 U.S.C. 154(b) by 178 days.

(21) Appl. No.: 16/304,293

(22) PCT Filed: May 25, 2016

(86) PCT No.: PCT/EP2016/000866
§ 371 (c)(1),
(2) Date: Nov. 25, 2018

(87) PCT Pub. No.: WO2017/202437
PCT Pub. Date: Nov. 30, 2017

(65) Prior Publication Data
US 2019/0083238 A1    Mar. 21, 2019

(51) Int. Cl.
*A61F 2/24* (2006.01)
(52) U.S. Cl.
CPC ............ *A61F 2/246* (2013.01); *A61F 2/2463* (2013.01); *A61F 2230/0093* (2013.01); *A61F 2250/0003* (2013.01)
(58) Field of Classification Search
CPC ............ A61F 2/246; A61F 2/2463; A61F 2230/0093; A61F 2250/0003
See application file for complete search history.

(56) References Cited

U.S. PATENT DOCUMENTS 5,944,738 A * 8/1999 Amplatz ............ A61B 17/0057
606/213
8,715,300 B2 * 5/2014 Najafi ................... A61B 5/0215
606/142
(Continued)

FOREIGN PATENT DOCUMENTS

CN          101056596    10/2007
EP           2478868     7/2012
WO      WO 2017/202437  11/2017

OTHER PUBLICATIONS

International Preliminary Report on Patentability dated Dec. 6, 2018 From the International Bureau of WIPO Re. Application No. PCT/EP2016/000866. (8 Pages).
(Continued)

*Primary Examiner* — Julian W Woo

(57) ABSTRACT

The invention relates to a heart implant comprising a tubular attachment element (1) for attaching a sheath, particularly having a sheath being coaxially positioned around at least a part of the tubular attachment element (1) and fixed to it, the tubular attachment element (1) having a lower end (1a) and an upper end (1b) and being split into several strips (2) at the upper end (1b), the strips (2) forming an expandable cage (C), particularly for fixing the heart implant to the atrium of the heart by surface contact between an exterior surface of the expandable cage (C) and an interior atrium surface, wherein in an expanded state the strips (2) extend from the upper end (1b) towards the lower end (1a) of the tubular attachment element (1) and form an expanded cage (C) being positioned around at least an upper part of the tubular attachment element (1).

15 Claims, 18 Drawing Sheets

(56) References Cited

U.S. PATENT DOCUMENTS

| | | | |
|---|---|---|---|
| 9,610,180 B2* | 4/2017 | Cam | A61B 17/12145 |
| 9,962,164 B2* | 5/2018 | Losordo | A61F 2/82 |
| 2005/0065589 A1* | 3/2005 | Schneider | A61B 17/0057 |
| | | | 607/126 |
| 2007/0198075 A1* | 8/2007 | Levy | A61F 2/82 |
| | | | 623/1.11 |
| 2009/0005656 A1* | 1/2009 | Najafi | A61B 5/686 |
| | | | 600/301 |
| 2010/0228279 A1* | 9/2010 | Miles | A61B 17/12159 |
| | | | 606/198 |
| 2015/0202043 A1 | 7/2015 | Zakai et al. | |
| 2018/0000585 A1* | 1/2018 | Solem | A61F 2/2403 |

OTHER PUBLICATIONS

International Search Report and the Written Opinion dated Feb. 1, 2017 From the International Searching Authority Re. Application No. PCT/EP2016/000866. (10 Pages).

Notification of Office Action and Search Report dated Mar. 2, 2020 From the State Intellectual Property Office of the People's Republic of China Re. Application No. 201680087184.7 and Its Translation of Office Action Into English. (7 Pages).

Notification of Office Action dated Jul. 23, 2020 From the State Intellectual Property Office of the People's Republic of China Re. Application No. 201680087184.7 and Its Translation Into English. (6 Pages).

* cited by examiner

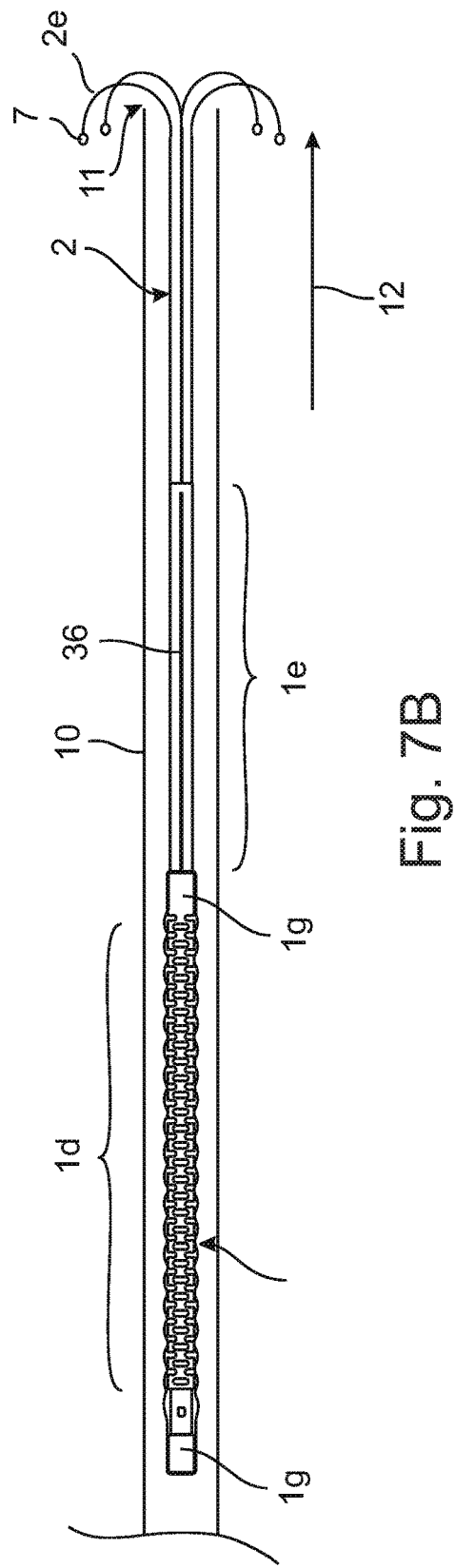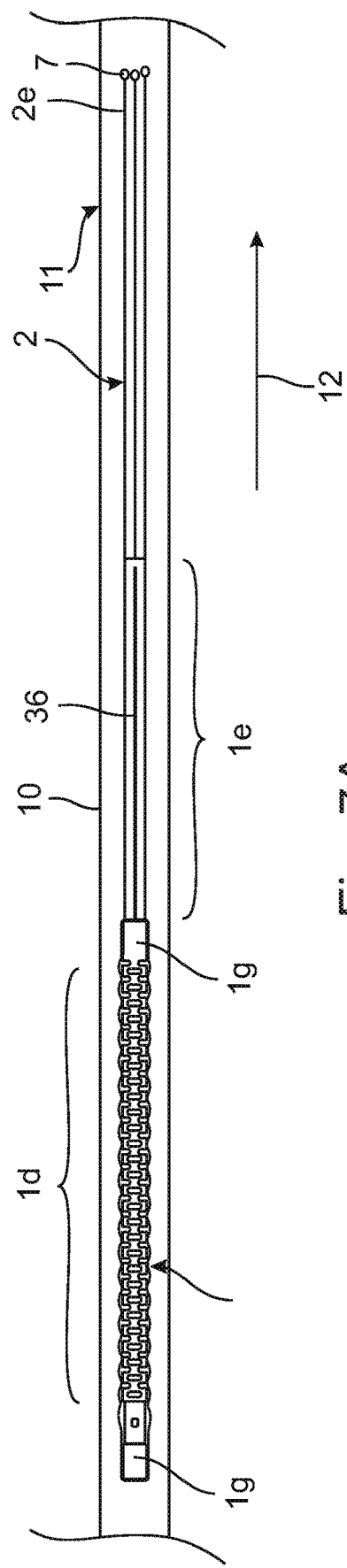

HEART IMPLANT

RELATED APPLICATION(S)

This application is a National Phase of PCT Patent Application No. PCT/EP2016/000866 having International filing date of May 25, 2016. The contents of the above application are all incorporated by reference as if fully set forth herein in their entirety.

FIELD AND BACKGROUND OF THE INVENTION

The invention relates to a heart implant, particularly a heart implant being configured to reduce or eliminate a heart valve insufficiency after implantation into the heart.

Typically such implants are positioned in such a way that a closure element of the implant is situated in the valve annulus and closes a remaining gap of the closed valve leaflets. For that purpose the closure element is connected to an anchoring element being configured to fix the closure element within the heart in the desired position i.e. in the valve annulus preferably to be contacted by the closing valve leaflets.

It is known in the art to use an anchoring element punctured into the myocardium of the ventricle for fixation of the closure element. Besides this invasive way modern implants provide a less invasive fixation just by contacting the interior wall of the atrium with the outer surface areas of an anchoring element formed of an expanded cage that is connected to the closure element. Such cage typically is in a collapsed state for feeding the entire implant through a catheter into the heart where it is expanded after release from the catheter for fixation purposes. The invention relates to such implants having an expandable, preferably mesh-like cage formed of strips for anchoring purposes. A cage may also be formed without meshes, particularly just by several side-by-side-lying strips having no interconnection. The invention in general also relates to non-meshed cages.

Applicants own patent applications having the serial numbers DE 10 2015 005 934.3 and EP 16000475.0, which are prior filed and post published already disclose a heart implant comprising a tubular attachment element for attaching a sheath to it. In these documents the sheath is formed of an inflatable membrane. After attaching, particular fluid tight attaching an inflatable membrane that may be inflated by a liquid the expanded membrane and the tubular attachment element surrounded, preferably coaxially surrounded by the membrane form the aforementioned closure element that is to be positioned in the respective heart valve annulus. The membrane may be made of a flexible or elastic material, preferably a foil. An expanded membrane encircles a space surrounding the tubular attachment element that reduces or eliminates a gap between the leaflets.

The implant furthermore described in this disclosure may generally comprise a sheath attached to the tubular attachment element, thus forming the closure element to be positioned within the valve annulus. In a possible embodiment the sheath may be formed of an inflatable membrane as known in the mentioned documents.

It is furthermore known from these documents that the tubular attachment element has a lower end and an upper end and is split into several strips at the upper end, the strips forming an expandable cage, particularly for fixing the heart implant to the atrium of the heart by surface contact between an exterior surface of the expandable cage (the several strips) and an interior atrium surface.

The mentioned positions "lower" and "upper" or directions mentioned in this disclosure are to be understood in the intended position of the implant if it is correctly implanted in the heart. In the heart the atrium is positioned above the ventricle and accordingly the lower end of the attachment element faces the ventricle, particularly is positioned in the ventricle and the upper end faces the atrium, particularly is positioned in the atrium if correctly implanted.

According to the teaching of these documents the several cage forming strips extend away from the attachment element towards the top of the atrium and form the expandable or expanded cage along their extension. Accordingly the anchoring cage formed by these strips is positioned entirely above the upper end of the attachment element and above the closure element formed by the attachment element and the sheath/inflatable membrane.

In view of the fact that the tubular attachment element and the strips may originate from one single tube by cutting the tubular wall several times, preferably in an axial direction the mentioned strips all start their extension from an annular upper end area of the attachment element and preferably are equally spaced along the circumference of this end.

The cage is formed by splitting and merging strips thus forming a half mesh between the points of splitting and merging. This embodiment is also preferred for the invention described in this disclosure.

A cage having several meshes is formed that way for solely fixing the heart implant to the atrium of the heart by surface contact between the exterior cage surface and the interior atrium surface.

A cage being formed of several expanded strips originating from a cut tube by radial expansion, particularly according to the aforementioned construction provides the advantage that the strips may generate a radial force (being essentially perpendicular to the axis of extension of the tubular attachment element) to keep the anchoring cage in place after implantation and expansion. The anchoring cage is sufficiently compliant in radial direction in order to adapt its shape to the atrium.

But furthermore the known anchoring cage is also compliant in axial direction of the tubular attachment element or the closure body formed by it due to the fact that in the expanded state the flexible strips of the cage are entirely positioned above the attachment element and the fact that an axial force may be split into radial force components due to the diverging strips. Such axial compliance may be regarded as unfavorable in particular cases.

It is therefore an object of the invention to provide a heart implant for mammalian patients, preferably humans, having a desired stiffness in axial direction (axis of the tubular attachment element after implantation or the connecting direction between ventricle and atrium), particularly having a higher axial stiffness in relation to the implant as known in the aforementioned documents. Furthermore even with improved axial stiffness the implant should be implantable by pushing the entire device though a catheter.

Accordingly it is an object of the invention to provide an implant having sufficient flexibility to follow the curved internal pathway of a catheter if pushed from the proximal side, i.e. the side of the implant facing away from the implantation site when the implant is positioned in the catheter. It is also an object of the invention to provide a method of treatment for preventing or at least reducing blood regurgitation in a diseased heart.

Even though the application of the implant and method is preferred in regard to humans the implant and method of treatment may be also applied to animals, particularly mammalian animals.

SUMMARY OF THE INVENTION

The object is solved by an implant comprising a tubular attachment element for attaching a sheath, particularly having a sheath, preferably an inflatable membrane being coaxially positioned around at least a part of the tubular attachment element and fixed to it, the tubular attachment element having a lower end and an upper end and being split into several strips at the upper end, the strips forming an expandable cage, particularly for fixing the heart implant to the atrium of the heart by surface contact between an exterior surface of the expandable cage and an interior atrium surface, wherein in an expanded state the strips, particularly all strips, extend from the upper end towards the lower end of the tubular attachment element and form an expanded cage being positioned around at least an upper part of the tubular attachment element. It is preferred in this invention, that the cage formed of the strips is the only anchoring means to fix the implant within the heart.

In contrast to the implants known from the aforementioned documents the strips do not form a cage being positioned entirely above the upper end of the tubular attachment element but form a cage surrounding the tubular element, particularly its upper part.

Preferably a predominant part of the cage surrounds the tubular attachment element. "Predominant" shall be understood in a way that the attachment element is surrounded by at least 51%, preferably at least 75% and even more preferred at least 85% of the cage in regard to the height of the cage, the height being regarded in the direction of the axial extension of the tubular attachment element. The height is preferably measured between a lower tangential plane contacting the lowermost part of the cage and an upper tangential plane contacting the uppermost part of the cage, both planes being perpendicular to the central axis of the attachment element.

Consequently the cage formed by the strips may have a minor upper cage part being convex to the heart wall of the atrium that is positioned above the upper end of the tubular attachment element from which the strips emerge.

This construction facilitates to prolongate the tubular attachment element in relation to the embodiments known from the mentioned documents. Accordingly the upper end of the tubular attachment element may be positioned very close to the top of the atrium. This provides an improved axial stiffness of the entire device due to the high axial stiffness of the tubular attachment element and the fact that the axial flexibility of the strips may only allow axial movement in the strongly reduced area between the upper end of the tubular element and the top of the atrium.

In a preferred embodiment the axial length of the tubular attachment element measured between lower end and upper end may be chosen to be longer than the distance between the valve annulus of the mitral valve and the top of the atrium. From a set of implants having different lengths of the attachment elements a best fitting one may be selected for an individual patient. In absolute values the length may be preferably chosen to be more than 50 mm, particularly if the implant is used for humans.

In order to provide the necessary radial compliance the cage may be formed in such a way that a (each) strip along its extension from the upper end of the tubular attachment element towards the lower end of the tubular attachment element or lower end of the cage comprises split strip regions in which the strip branches into two strips and merged strip regions, in which two strips, in particular respectively formed of a strip split beforehand, are merged into one strip.

Splitting and merging may be performed at least two times, particularly exact three times, along the strip extension from the upper end towards the lower end. Extending towards the lower end does not necessarily mean that the strips or cage formed by the strips end at the lower end of the tubular attachment element. Preferably the lower end of the respective strips or the lower end of the formed cage end in a height above the lower end of the tubular attachment element.

The cage forming by the strips may start at the upper end of the tubular attachment element with splitting each single strip emerging from the upper end or with merging two respective neighboring strips, each one of the two strips emerging from the upper end.

Particularly in such a construction the number of strip ends, each being formed of the last merged strip region or last split strip region at the end of extension corresponds to the number of strips emerging from the upper end of the tubular attachment element. Such embodiment is preferred in order to minimize the number of strip ends, particularly if cage forming starts with splitting of strips. Of course in such embodiment it is also possible to provide strip ends formed of branches at the end of extension of the cage leading to a doubled number of strip ends compared to the number of strips at the upper end of the tubular attachment element.

A split strip region, preferably formed by laser cutting a strip in the axial direction, may have a cross section being smaller than the cross section of a merged strip region (measured perpendicular to the extension), preferably half the cross section or less than half the cross section of a merged strip region. Accordingly the flexibility of the thinner split strip region is higher than the flexibility of the thicker merged strip regions.

Preferably the flexibility of the thinner split strip regions may be at least a factor 2 higher than the flexibility of the merged strip regions. Such flexibility may be understood as being complimentary to stiffness (preferably meaning that flexibility is proportional to 1/stiffness), which is the extent to which the two different regions resist deformation in response to an applied force.

For example applying the same force to a split strip region and a merged strip region will in this case result in a higher deformation in the split strip region compared to the deformation in the merged strip region. Consequently the invention provides that the radial flexibility/compliance of the entire cage may be chosen very high. Nonetheless this does not significantly influence the needed axial stiffness in view of the fact that the strips and their different regions are predominantly contacting the inner heart wall of the atrium after implantation and accordingly almost cannot not move along the line of contact.

Splitting a strip into to two split strip regions and merging side-by-side lying split strip regions of two different former neighboring strips may be achieved by cutting slits into the wall of a tube, the slits being spaced in axial direction and axially offset (interdigitated) in circumferential direction.

In this context it is preferred to provide that along the extension from the upper end of the tubular attachment element towards a strip end (preferably formed of merged strip regions at the end of extension) the sum of the length of all split strip regions lying along this way is bigger than the sum of the length of all merged strip regions along the same way.

It may be provided according to the invention that at least the tubular attachment element and all strips or the different strip regions are formed of the same tube by cutting the tube wall. Such tube may be formed of nitinol as an example. It is also possible to form only the strips of a single tube, preferably a metallic tube, like nitinol tube and to attach that to another tubular element being formed of another tube, preferably of another material, particularly PEEK (Polyetheretherketone) or PET (Polyethylenterephthalate). The different tubes may be fused together to form a tubular attachment element.

The invention allows a treatment of heart valve insufficiency in which the collapsed implant according to the invention may be introduced into a placed catheter, an end of which being positioned in the heart, preferably through the valve annulus in the atrium of a mammalian patient, preferably a human. The implant will be pushed through the catheter by applying a pushing force to the end of the implant facing away from the implantation site. The implant is propagated through the catheter until it is released from it into the heart, preferably into the atrium, where it is expanded from the collapsed state to an expanded state for fixation purposes.

Expansion of the cage may be performed automatically after release out of the catheter in view of the fact that the implant/cage is in a first embodiment heated to body temperature due to blood contact and thus expands into the teached-in shape of the shape memory material of the cage or in a second embodiment merely due to the superelasticity of the chosen cage material, like nitinol.

Fixation is performed in a way that a sheath that is attached to the tubular attachment element is positioned within the valve annulus preferably such that the closing leaflets get into contact with the exterior surface of the sheath. In case the sheath is chosen to be an inflatable membrane its expansion may be done by filling the inner volume of the inflatable membrane with a fluid (gas/liquid) after fixation and positioning or also automatically, for example by means of an internal scaffold structure expanding the covering sheath due to the scaffold's own expansion, particularly by means of the same mentioned memory effect or superelasticity. Accordingly a blood regurgitation may be reduced by preventing or at least reducing the remaining gap between the leaflets.

The collapsed, also called crimped state of the implant is understood as a configuration of the implant in which it is suitable to propagate it through the inner free diameter of a catheter. Preferably in this collapsed state all strips and their split or merged regions are positioned within the exterior diameter of the tubular attachment element (regarded in a cross sectional view perpendicular to the central axis of the tubular attachment element).

Furthermore preferred an inflatable membrane connected to the tubular attachment element is unfilled in this collapsed state of the implant and wound around the tubular attachment element. A sheath supported by a scaffold structure underneath is also not expanded in that collapsed state in view of the fact that the scaffold structure is not yet expanded. Such scaffold structure may be formed of the tubular attachment element itself, or at least a part of it, as mentioned later.

The expanded state of the cage of the implant is a state of expansion, preferably at least slightly below maximum possible expansion of the cage, that is determined for fixation purposes. In this expanded state after implantation the cage tends to further expand and thus exerts a force to the inner heart wall, preferably of the atrium. Preferably such force has a predominant component in a direction radial to the center axis of the attachment element. Preferably in the expanded state of the entire implant also the sheath is expanded in this state, preferably by filling a fluid into it or other internal forces. Any possible states inbetween these mentioned states are understood as intermediate states having no particular relevance.

In an improved embodiment the strip ends at the end of extension form free strip ends, particularly in the expanded state of the cage the free strip ends being bent towards the central axis of the tubular attachment element and/or being bent towards themselves, particularly forming a loop over at least 200 degree. Such a bent configuration reduces the risk that a free strip end may puncture the heart wall during the implantation process.

A strip end of the cage may be understood as free if it is not constantly connected to another strip end or another permanent structure. But in a preferred embodiment the invention provides a construction in which the free strip ends are temporarily connected to each other, preferably during the process of implantation.

Preferably the free strip ends may be connected to each other with a pull wire at least temporarily or prior to expansion of the implant. Preferably such connection may be provided by the manufacturer of the implant and released after implantation. It is also possible that a person, preferably the surgeon will attach the pull wire to the free strips ends immediately prior to implantation. Such a wire may be formed of a metal wire or a textile wire, particularly by a suture filament. Such suture element may be bio-degradable.

For the purpose of connecting the free strip ends the wire may be guided through pinholes or orifices provided in the respective tips of the free strip ends or may be guided through loops formed in the free strip ends by bending. Such a pinhole/orifice may be formed by laser cutting/drilling, for example at the time of cutting the strips in the tube wall. In such a case the pinhole will not broaden the width of a free strip end measured perpendicular to its extension. It is also possible that an orifice is formed as a bail or eyelet having a width bigger than the preceding strip. If a loop if formed at a free strip end by bending the free strip end such loop needs not to be totally closed.

In the non-expanded state, particularly in a state in which the implant is positioned in a catheter, the cage forming strips and their different regions extent away from the upper end of the tubular attachment element in an axial direction pointing from to lower end to the upper end. Accordingly when placed in a catheter the free strip ends are all facing towards the implantation site.

During the process of pushing the implant through the catheter the strips that form the cage surrounding the tubular attachment element in the later expanded state and particularly their free strip ends are first released from the catheter, the free strip ends bend over the opening rim of the catheter, preferably away from the implantation site, by means of internal forces immediately after release thus forming the beginning of the cage.

Preferably the free strip ends are held together during this process by means of a connecting pull wire, being fed through loops or pin holes or other orifices of the respective free strip ends and through the catheter.

The implant is preferably furthermore pushed forward by simultaneously fixing the free strip ends in position or holding them close together near the catheter or retracting the free strip ends towards the catheter by means of applying a pulling force to the pull wire and pushing at least an upper tubular part of the tubular attachment element through an annular formation formed by the pull wire and the free strip ends. Preferably after releasing and furthermore after placing the implant in the correct position the pull wire is released from the free strips ends, preferably retracted out of each loop or pinhole/orifice and out of the catheter.

Such procedure provides the advantage that the free strip ends are held together by the pull wire during the implantation process. This keeps the cross section of the implant small until the pull wire is retracted and the cage fully expanded.

The invention may provide different embodiments of the tubular attachment element that are all combinable with the described construction of the cage and the implantation process.

In a first embodiment the tubular attachment element comprises—at least in the expanded state—a meshed lateral area. Such lateral area may be preferably formed of a cut/slotted tube that is radially expanded. In this embodiment the cage forming strips may be formed of a first part of a tube and the meshed lateral area of a second part of the tube.

Such meshed lateral area may extend between the lower end and the upper end over at least 90% of the distance between lower and upper end, preferably over the entire distance between lower end and upper end. Consequently in the latter version the entire tubular attachment element is meshed.

The meshed lateral area of the tubular attachment element may form a scaffold that supports the aforementioned sheath from underneath. The sheath may accordingly be expanded by expanding the underlying tubular attachment element. In such an embodiment sheath and scaffold have a direct contact.

In a second embodiment the tubular attachment element comprises a first axially extending lower tubular part being covered or at least coverable by a sheath and a second axially extending upper tubular part, preferably being external to the sheath, the upper tubular part extending between the first lower tubular part and the upper end of the tubular attachment element where the strips emerge.

In a preferred embodiment the lower tubular part may have a bigger cross section than the upper tubular part. Such lower tubular part may comprises a meshed lateral area, preferably is entirely formed of a meshed lateral area. Comparable to the embodiment mentioned before the meshed lateral area may be formed of an expanded cut/slotted part of a tube.

Also in this embodiment the meshed lateral area may form an internal scaffold of a sheath directly contacting the scaffold.

In all the mentioned embodiments in which a meshed part of the tubular attachment element is provided the sheath may be preferably formed of polymer fibers, particularly polyester fibers, particularly woven polymer/polyester fibers.

According to another embodiment the lower tubular part and the upper tubular part may also have the same cross section, i.e. diameter. The lower tubular part may be coaxially surrounded by an inflatable membrane that forms the sheath.

In the aforementioned embodiment in which the tubular attachment element is entirely meshed (at least in the expanded state) the attachment element provides inherent resilience and as such enough flexibility to follow the curvature of a catheter during implantation.

In the other embodiment, in which the attachment element comprises lower and upper tubular parts these two parts may provide the necessary flexibility by means of cuts being positioned in the lateral area of the respective tubular parts. Such cuts in the lower tubular part may form a mesh after expansion as mentioned.

The lower and the upper tubular flexible parts may be axially spaced by means of a rigid tubular part of the tubular attachment element, preferably the rigid part being formed of the original non-cut tube. Such the rigid tubular part may form an area of the tubular attachment element to which the upper part of a sheath, preferably of an inflatable membrane may be attached or is attached. Also the lower end of the tubular attachment element may comprise a rigid section in order to attach the lower part of an inflatable membrane or expandable sheath to it. A valve mechanism may be integrated in the lower rigid section.

The cuts in the lower tubular part and the cuts in the upper tubular part may be arranged in different cut patterns. The cut pattern in the lower tubular part may comprise straight cuts, particularly extending axially and/or in circumferential direction. The cut pattern in the upper tubular part may comprise at least one straight or helically extending cut.

Different cut patterns in the lower and upper part of the tubular attachment element provide the possibility to have different flexibility in these two parts. The flexibility is chosen to be high enough in order to push the collapsed implant through the curved catheter. But the flexibility of the upper part may be chosen to be smaller than the flexibility in the lower part in order to assure the intention of the invention to have improved axial stiffness and thus to reduce axial movability of the closure body formed of the sheath or inflatable membrane surrounding at least the lower part of the attachment element.

BRIEF DESCRIPTION OF THE SEVERAL VIEWS OF THE DRAWINGS

FIG. 7A illustrates a collapsed implant totally positioned in a catheter, the free ends of the strips facing to the implantation site FIG. 7B illustrates a collapsed implant positioned in a catheter, the free ends being first released from the catheter and bending over the catheter rim FIGS. 8A-E schematically illustrates the process of implantation in different temporal steps

DESCRIPTION OF SPECIFIC EMBODIMENTS OF THE INVENTION

Figure 1A:
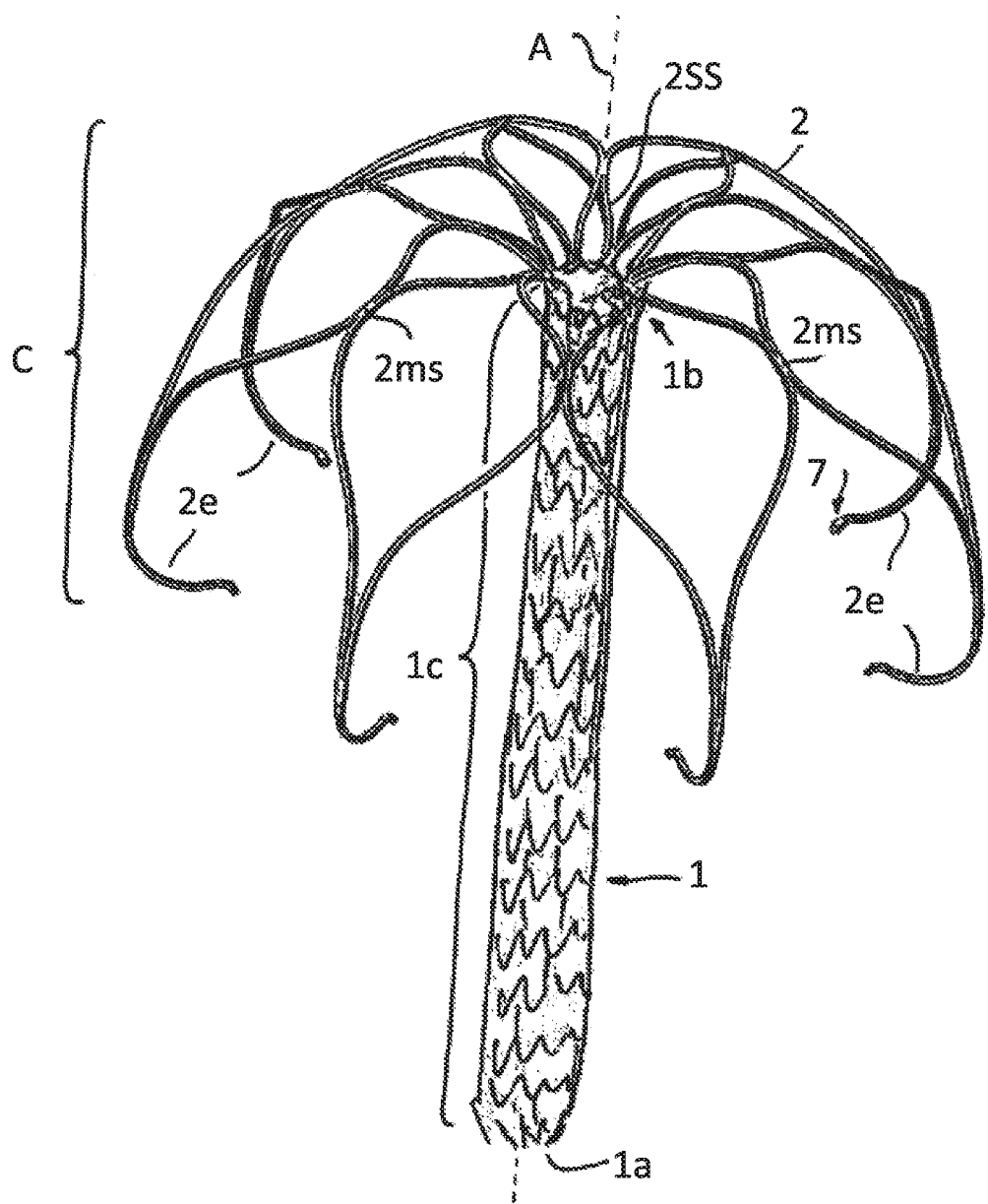
FIG. 1A illustrates a perspective view of an implant according to a first embodiment having a meshed expanded attachment element
Figure 1B:
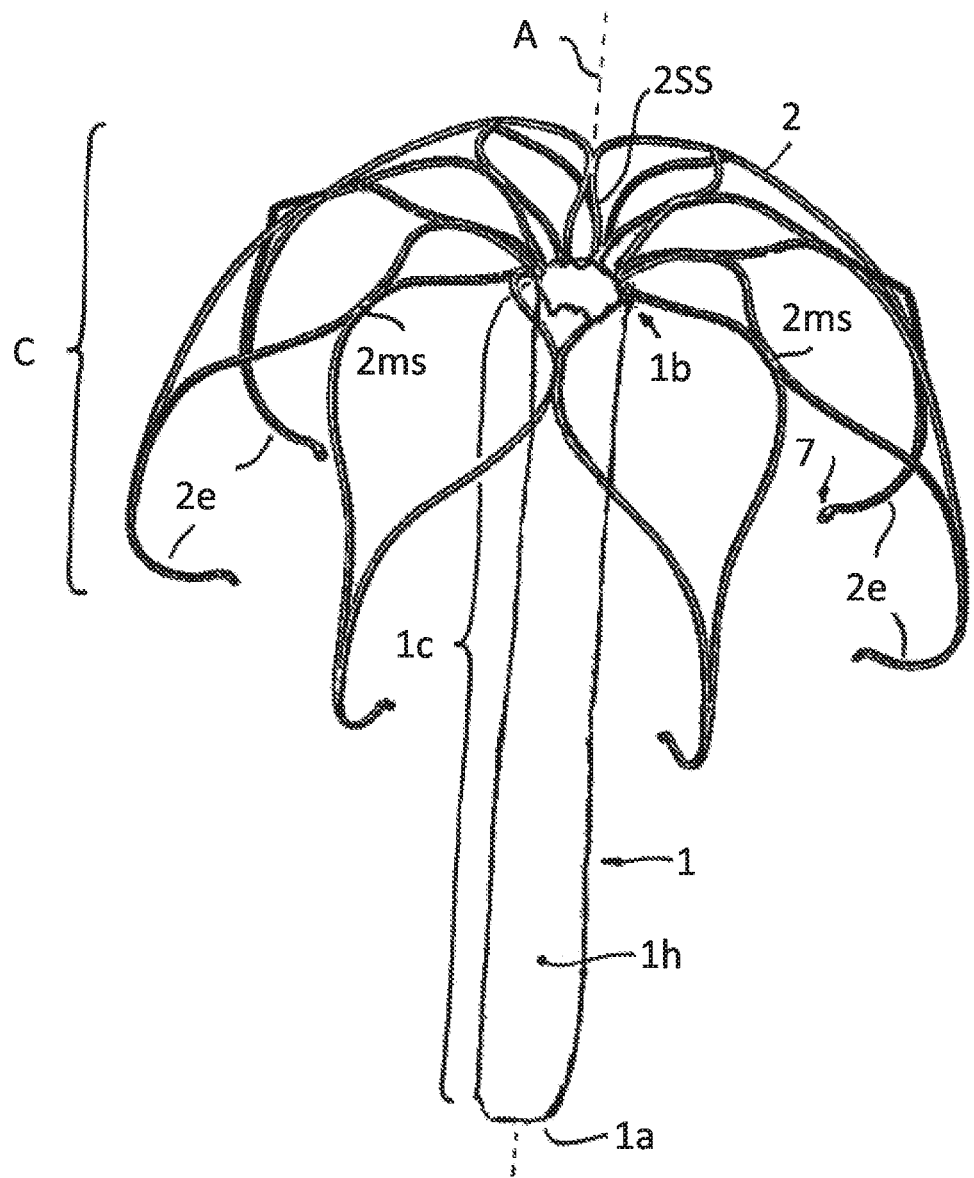
FIG. 1B illustrates the embodiment of FIG. 1A having a sheath covering the meshed expanded attachment element

FIG. 1 show a first embodiment according to which the implant comprises a tubular attachment element 1 having a lower end 1a and an upper end 1b. The entire attachment element 1 is formed as a mesh by a radially expanded slotted tube, particularly as known from a typical stent construction. FIG. 1A just shows schematically the meshes of the meshed expanded tubular attachment element 1. FIG. 1B shows the attached sheath 1h, that in this drawing hides the underlying meshes, that serve as a supporting scaffold. Even though it is not shown the meshes may have a honeycomb shape.

A sheath 1h that is attached to the attachment element 1 may be formed of polymer fibers, by example as known by the trade name DACRON. The fibers may form a woven textile. Such sheath 1h serves to form the contact area for not closing leaflets of the natural valve of a diseased heard.

In this and all other possible embodiments of the invention described before and hereinafter the upper end 1b of the attachment element 1 supports a cage C having a shape comparable to an umbrella that spans the attachment element 1.

The cage C is formed of several strips 2 emerging from the upper end 1b that are each split into two split strip regions 2ss. Neighboring spilt strip regions 2ss are recombined to merged strip region 2ms, the merged strip regions 2ms being split again into split strip regions 2ss and these ones being recombined to merged strips regions that—in this case—form respective free strip ends 2e. The free strip ends may have orifices or pinholes 7 in all embodiments, particularly for feeding a pull wire through the orifices and thus for temporarily connecting the free strip ends 2e.

FIG. 1 also show that the free strip ends 2e are bent towards the central axis A of the tubular attachment element 1 thus reducing the risk of puncturing the myocard.

In this embodiment more than 50% of the axial length of the tubular attachment element 1 is surrounded by the cage C.

Figure 2A:
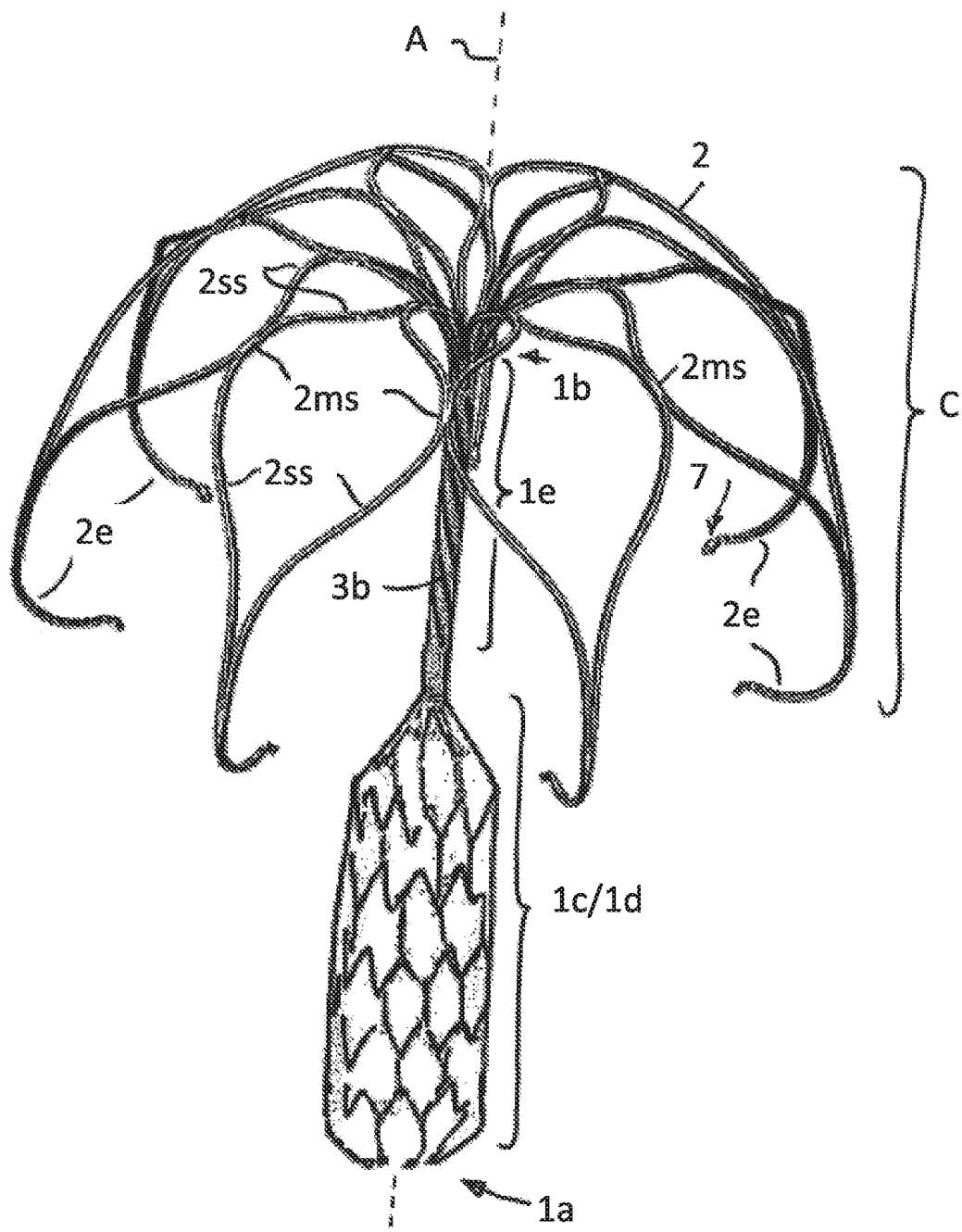
FIG. 2A illustrates a second embodiment having just the lower part of the attachment element meshed and expanded and the upper part slotted/cut
Figure 2B:
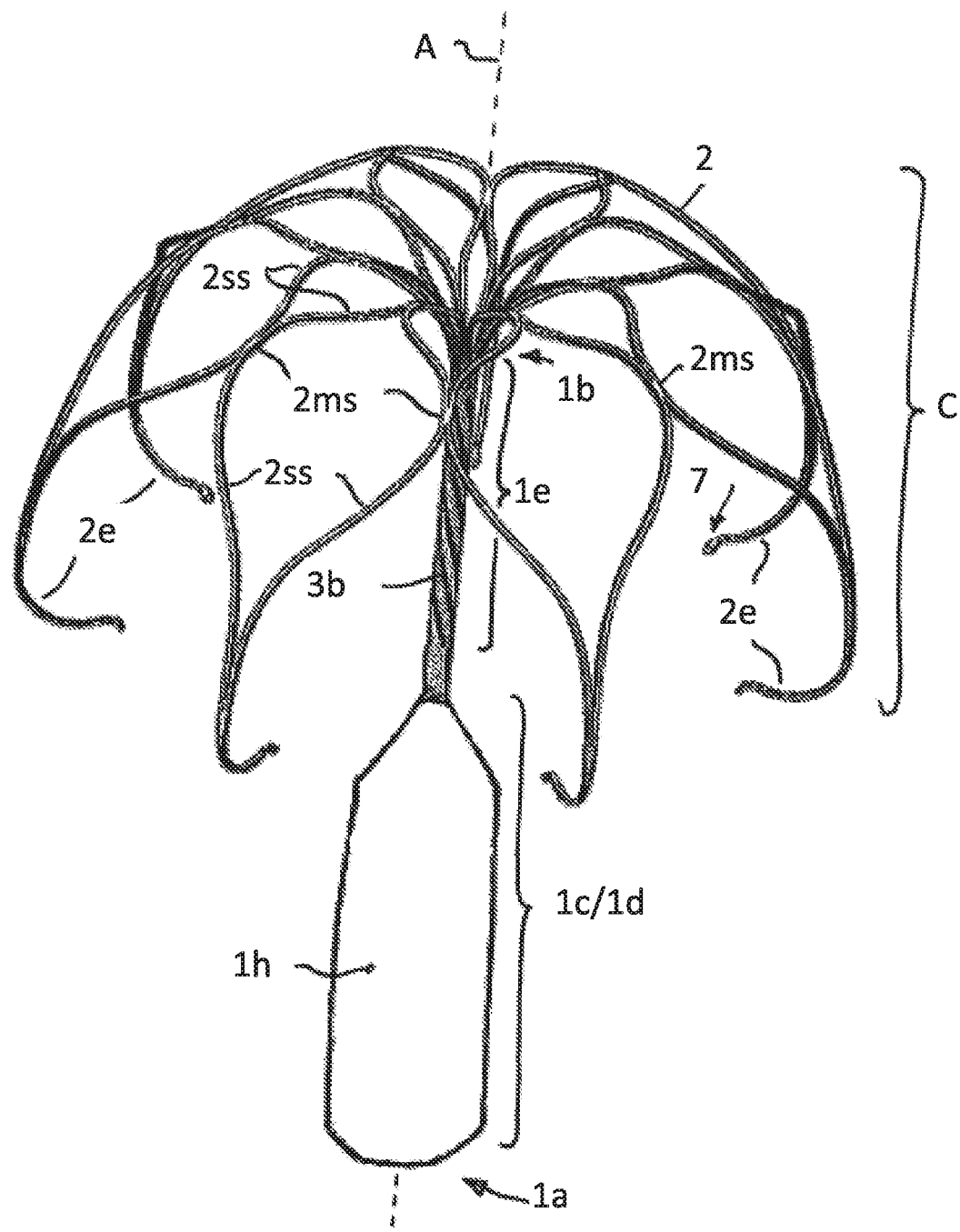
FIG. 2B illustrates the embodiment of FIG. 2A having a sheath covering only the meshed lower part of the attachment element

FIG. 2 show a different embodiment having the same cage construction as shown in FIG. 1. Here the tubular attachment element 1 comprises a lower tubular part 1d and an upper tubular part 1e. The lower part 1d has a bigger cross section compared to the upper part 1e in view of the fact that the lower part is formed by expanding a slotted area of a tube. Slotting is performed in such a way that a meshed scaffold is formed that also in this embodiment supports a sheath, preferably having the features as described for FIG. 1. FIG. 2A shows the meshes of the lower tubular part 1d without sheath. FIG. 2B shows the sheath 1h contacting the meshes and thus hiding the meshes. The sheath ends at the lower end of the upper tubular part 1e. In another embodiment—not shown—the sheath may also cover the upper tubular part 1e of the attachment element 1, but is not expanded in that area.

In order to provide a flexibility needed for the implantation process also in the upper tubular part 1e this part is also slotted with cuts, but having a different cut pattern. Here the cut pattern provides at least 2 helically wound cuts 3b.

The embodiment of FIG. 2 provides a higher axial stiffness compared to the embodiment of FIG. 1.

Figure 3:
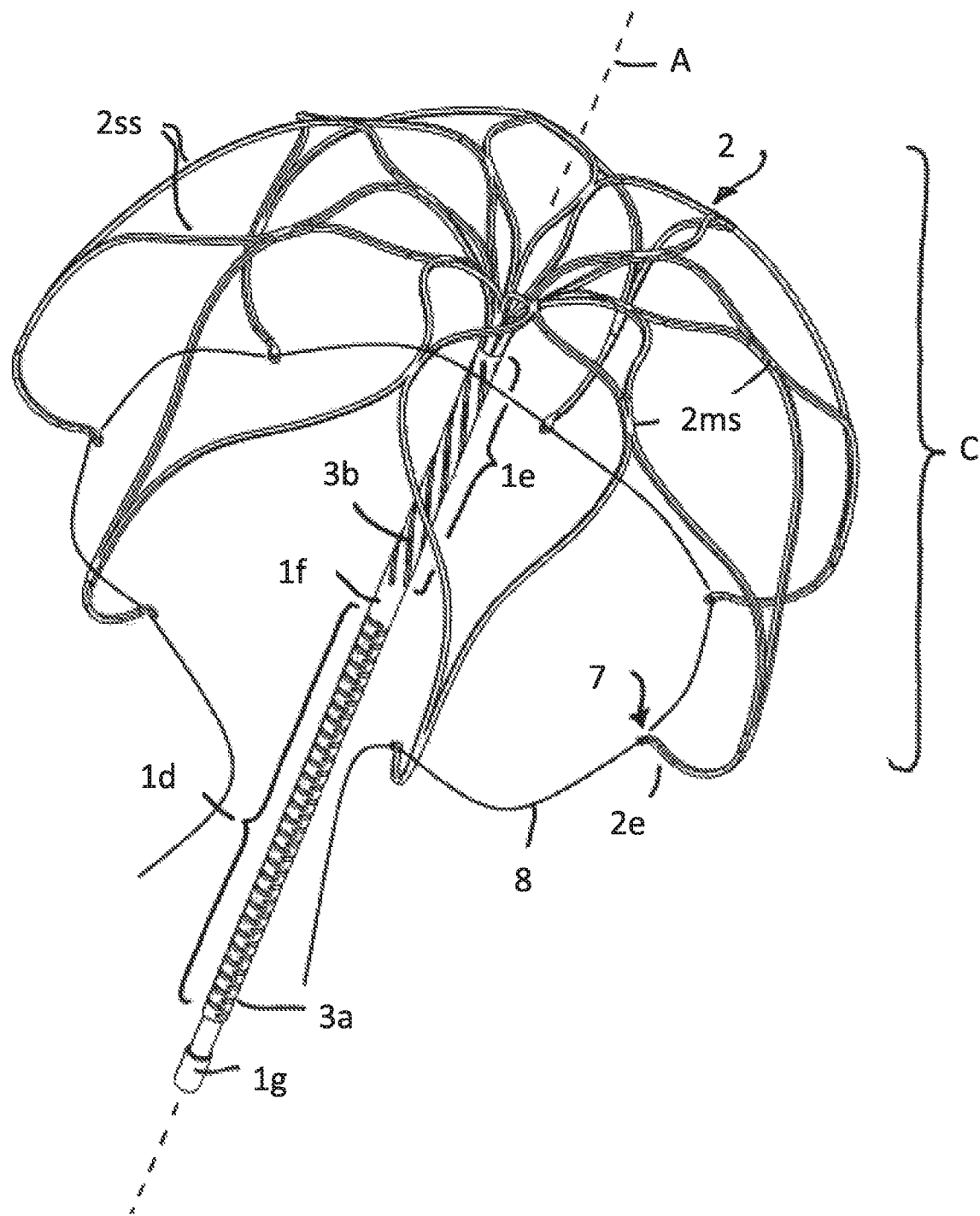
FIG. 3 illustrates a perspective view of a third embodiment having the attachment element divided in a lower and upper part with different cuts/slotting

It can be seen in FIG. 2 that the lower end of the cage C formed by the bent free strip ends 2e is positioned below the lower end of the upper tubular part FIG. 3 shows a different embodiment having again the same cage C as shown in FIGS. 1 and 2. In contrast to the FIGS. 1 and 2 the embodiment of FIG. 3 is intended to attach an inflatable membrane to the attachment element 1 that also has a lower tubular part 1d and an upper tubular part 1e, both being separated from each other by a rigid tubular part 1f. The rigid tubular part 1f and the lowermost rigid tubular part 1g serve to attach the lower and upper ends of the inflatable membrane. The upper tubular part 1e is positioned above the membrane that is not shown here. A membrane is instead shown in connection with FIGS. 4B and 4C having the same lower tubular part 1d. The same construction may apply here in the embodiment of FIG. 3.

Also in this embodiment the lower and upper tubular parts have different cut pattern to provide flexibility but different axial stiffness in the two parts. The upper part 1e comprises at least two helically wound cut 3b, as also shown in FIG. 2.

The lower part 1d comprises pairs of opposing straight cuts 3a, along the axial direction A the pairs having alternating different cut directions (with regard to the circumferential angle). For example a first cut of the first pair is positioned at an angle of 0 degree and the second cut of the first pair is positioned opposite at an angle of 180 degree. Axialy offset follows a next pair of cuts, the first cut being positioned at an angle of 90 degree and the second opposite at an angle of 270 degree, and so on. Accordingly axially successive pairs of cuts have an angular offset of 90 degrees in circumferential direction.

FIG. 3 also shows that the free strip ends 2e have each a pinhole 7 in the respective tips. A pull wire 8 may be fed through the pinholes 7 for implantation purposes as described later. In all embodiments that comprise pinholes or other orifices or loops in the free end strips the pinholes/ orifices/loops may have an opening plane being parallel to the axis A of the tubular attachment element 1. This facilitates pulling the wire 8 out of the pinholes 7 or orifices/loops after implantation since the pulling force along the wire extension is in that case always essentially perpendicular to the opening plane.

FIG. 4 show an embodiment in which free strip ends 2e of the cage-forming strips 2 are bent towards themselves in a plane parallel to the axis A of extension of the tubular attachment element 1 thus forming a respective loop 6 that extends over at least 200 degrees. The loops 6 serve to reduce the risk of puncturing the myocards and may also be used to feed a pull wire (not shown here) through it.

In comparison to FIG. 3 the upper tubular part 1e of the tubular attachment element 1 comprises straight axial cuts 3b, particularly providing more axial stiffness compared to helical cuts. The lower end of the cage C or the free end strips 2e are positioned above the lower tubular part of the attachment element 1, particularly above the rigid tubular part 1f or on the same height of it.

Figure 4A:
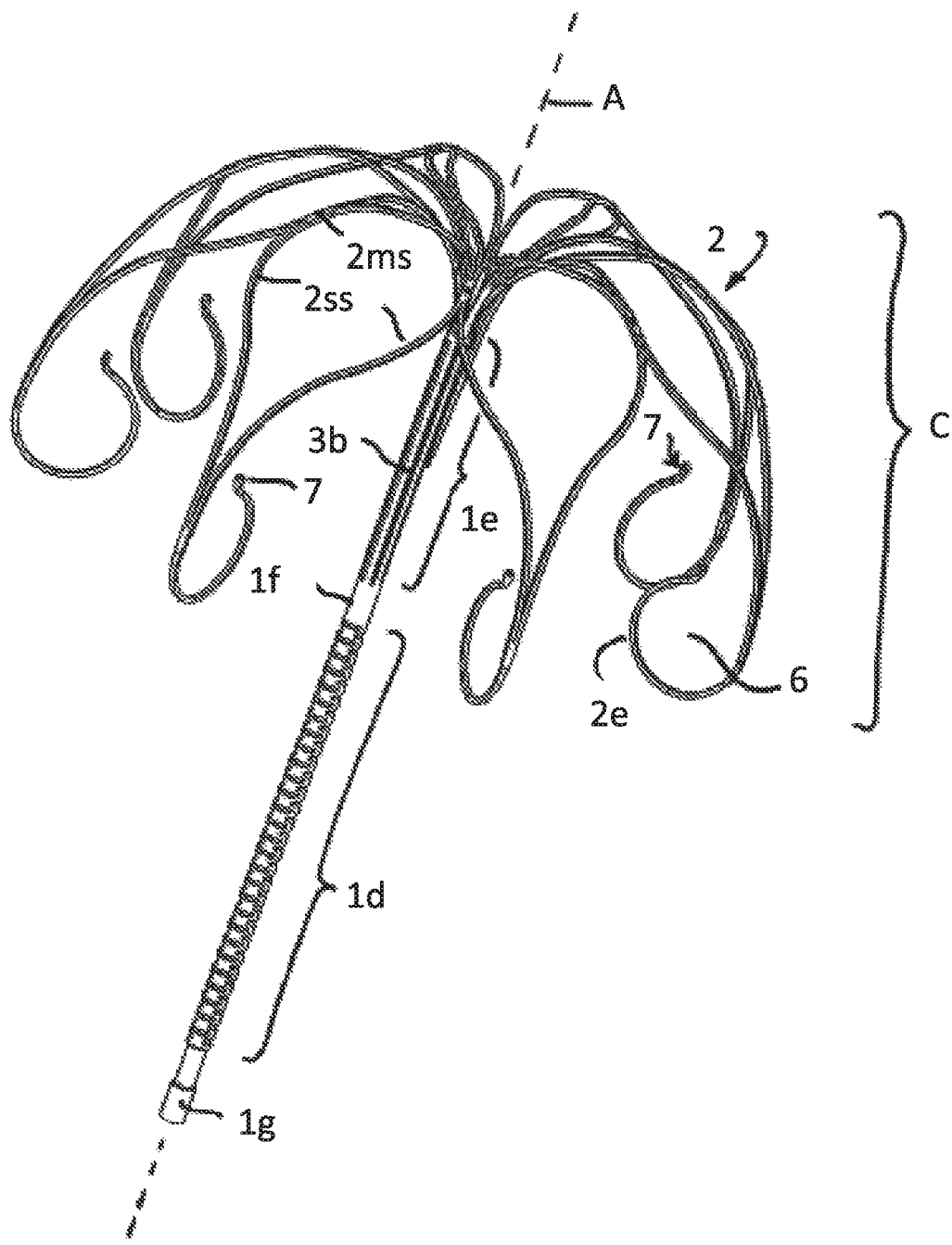
FIG. 4A illustrates a perspective view of a fourth embodiment having the attachment element divided in a lower and upper part with different cuts/slotting
Figure 4B:
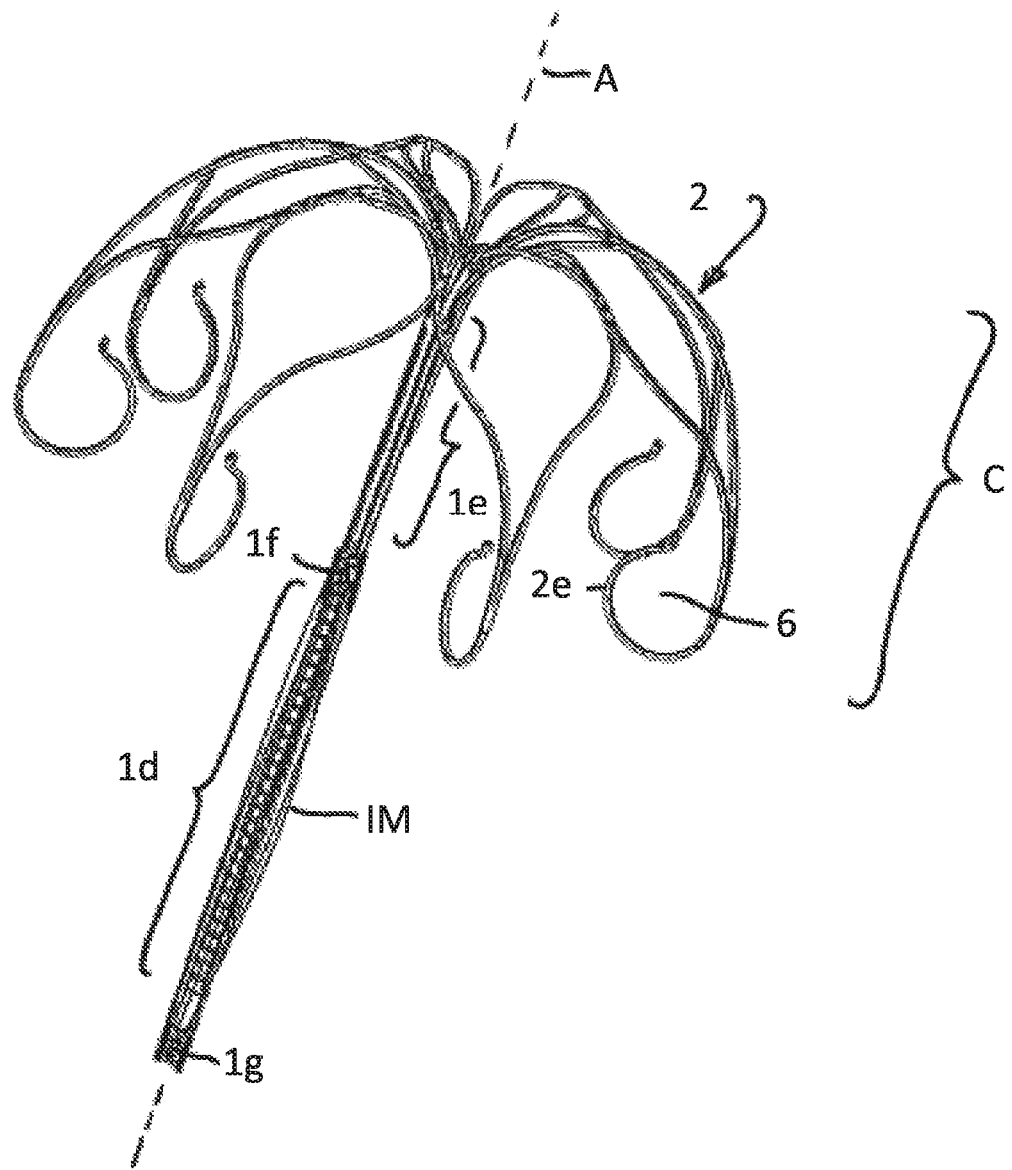
FIG. 4B illustrates the embodiment of FIG. 4A having a deflated sheath attached to the lower part of the attachment element
Figure 4C:
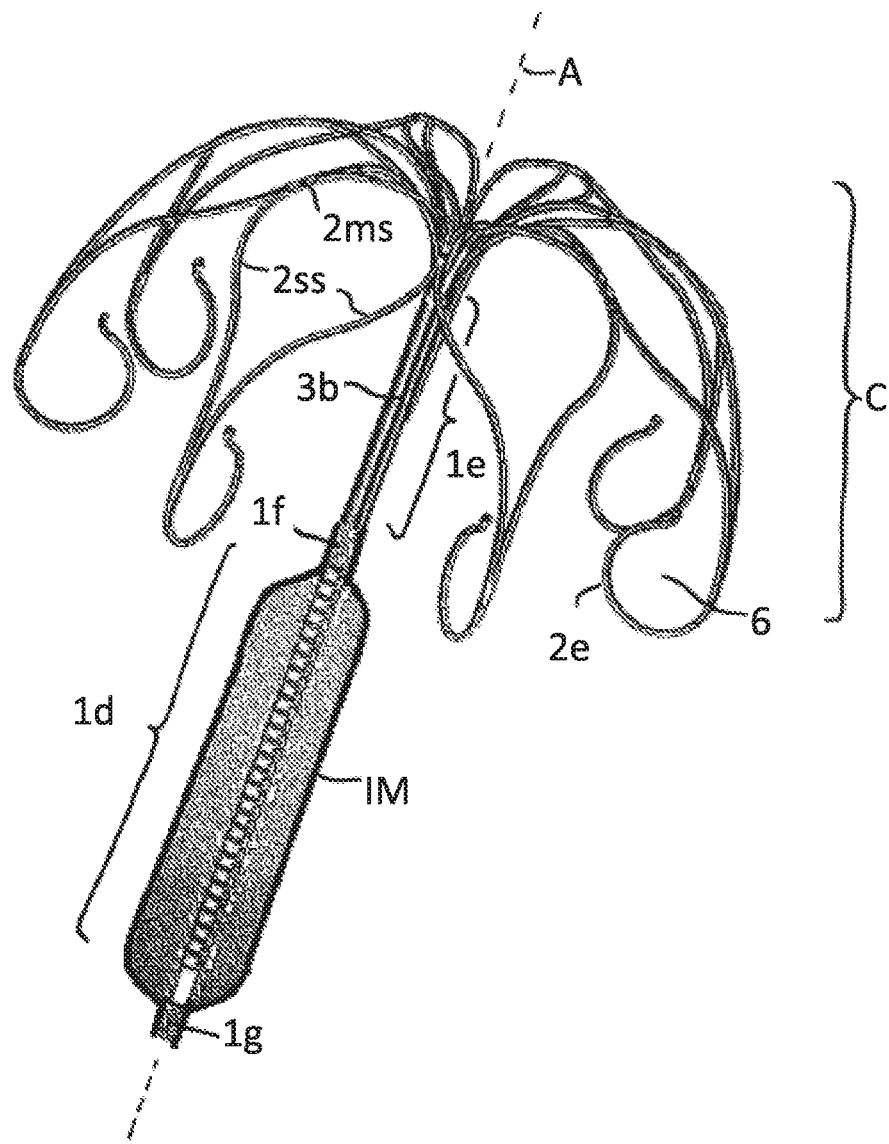
FIG. 4C illustrates the embodiment of FIGS. 4A and 4B having an inflated sheath

FIG. 4A shows the implant without an attached inflatable membrane. FIG. 4B shows a deflated inflatable membrane IM, that surrounds the lower tubular part 1d only and is fixed to the rigid part 1g and 1f. FIG. 4C shows the same embodiment after inflation of the membrane IM.

Figure 4D:
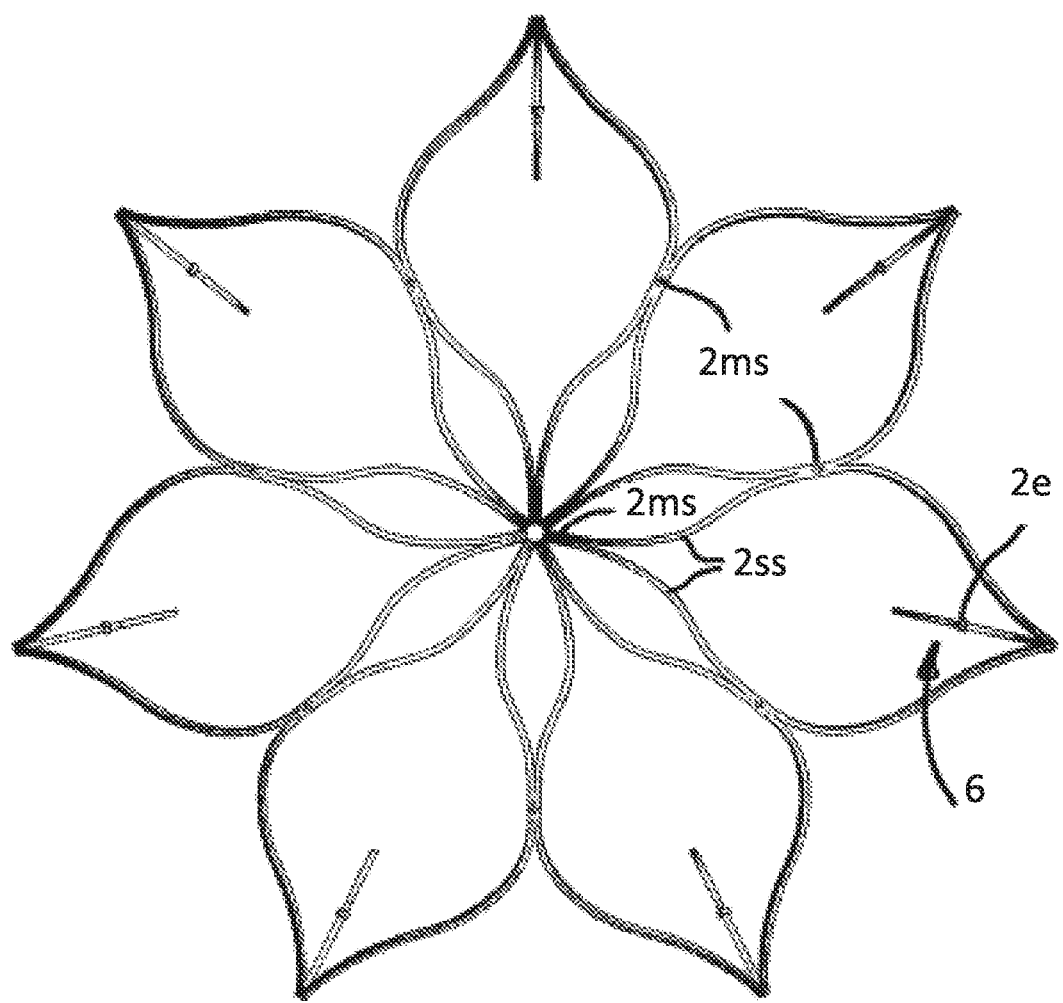
FIG. 4D illustrates a top view of the cage formed by the strips of all embodiments of FIGS. 4A-C

FIG. 4D shows a top view of the cage C depicting that the strips 2 start with a merged strip region 2ms, that is split into two split strip regions 2ss, merged again, split again and last time merged to form the free strip end with the mentioned loop 6.

Figure 5A:
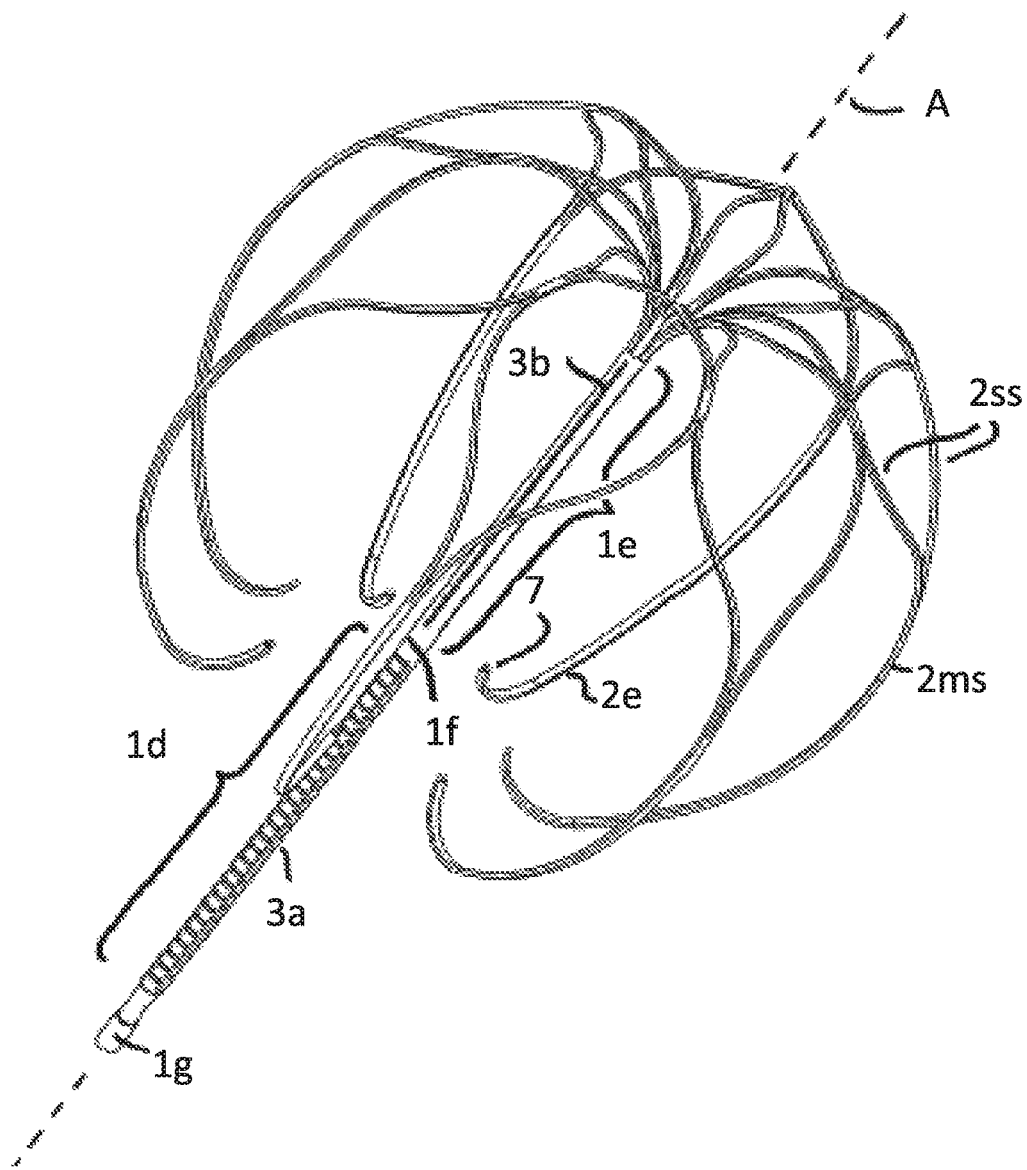
FIG. 5A illustrates a perspective view of a fifth embodiment having the same attachment element as FIGS. 4A-D but a different anchoring cage
Figure 5B:
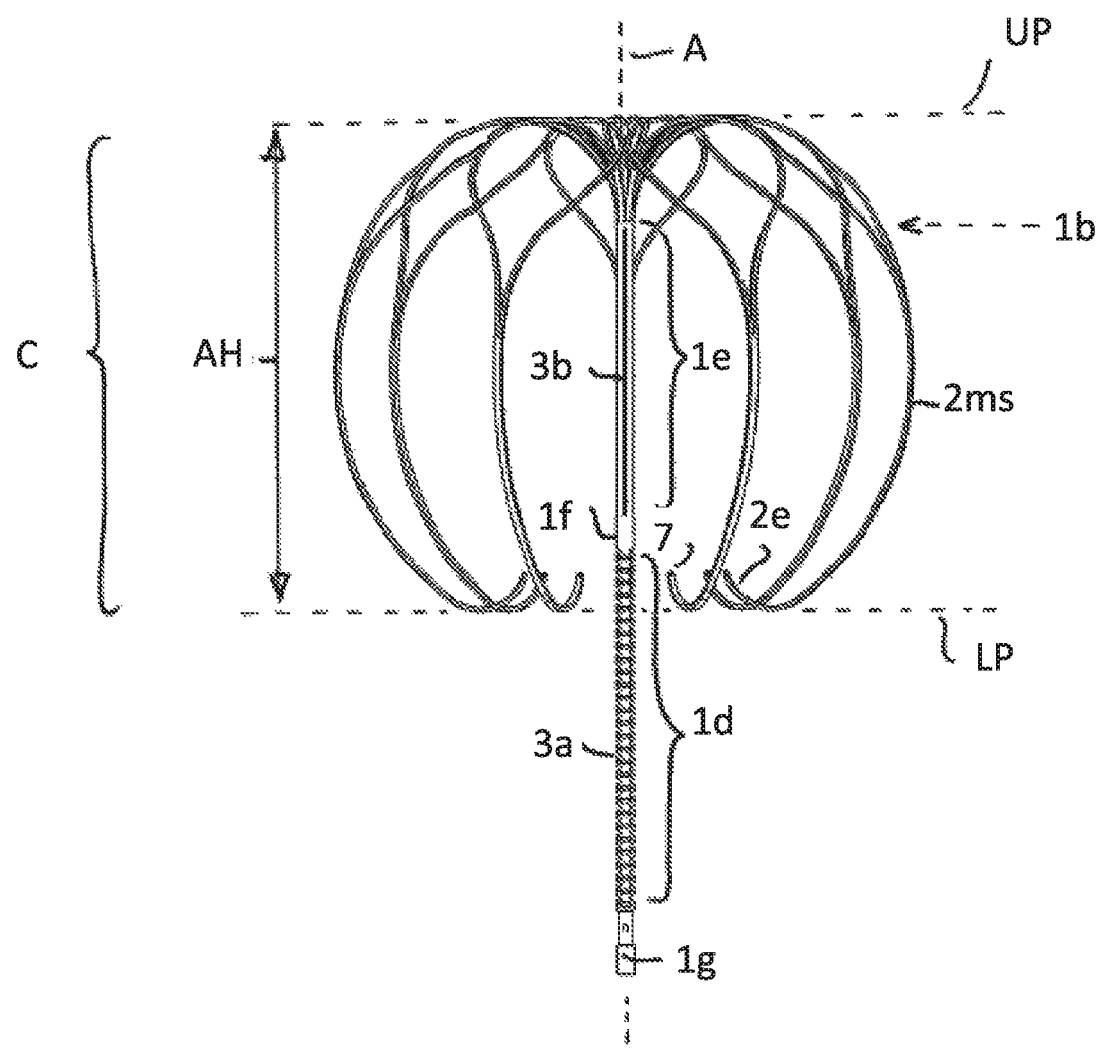
FIG. 5B is a side view of FIG. 5A

FIG. 5 show an implant having an attachment element 1 as also shown and described in FIG. 4. Irrespective of such construction the cage C has a bigger axial length (height) compared to FIG. 4. Here the lower end of the cage C or the free end strips 2e are positioned around the upper area of the lower tubular part 1d. The axial height AH of the cage C is accordingly bigger than 50% of the axial length of the attachment element 1. The height is measured according to FIG. 5B between a lower tangential plane LP and an upper tangential plane UP, each plane contacting the cage and being perpendicular to axis A. As can be seen in FIG. 5B by depicting the position of the upper tubular end 1b with a dashed arrow more than 75% of the cage C surrounds the tubular attachment element 1.

Figure 5C:
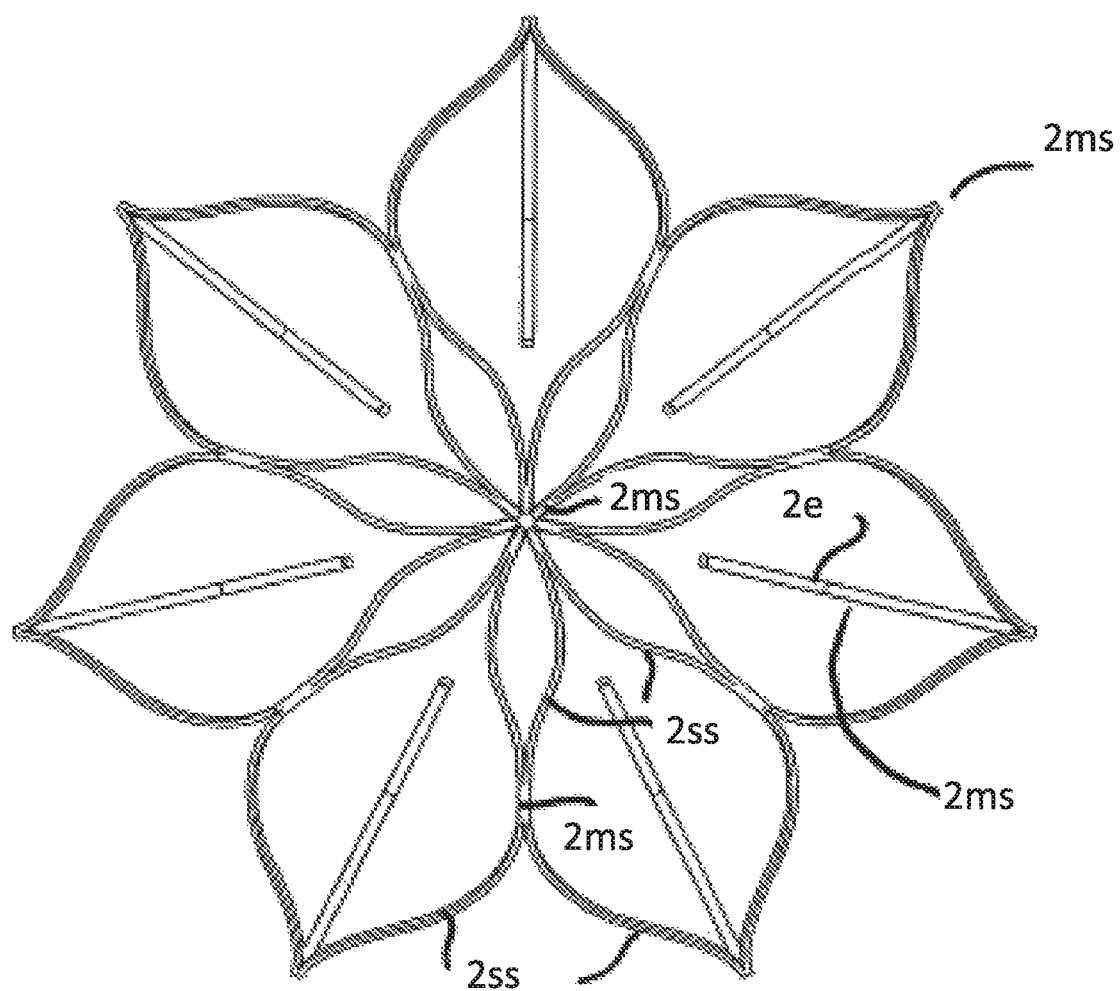
FIG. 5C is a top view of the cage of embodiments according to FIGS. 5A and 5B

FIG. 5A shows the perspective view of this embodiment and FIG. 5B the side view. FIG. 5C shows the top view of the cage C.

It is essential for this embodiment. irrespective of the specific construction of the tubular attachment element, and as such combinable with all possible attachment elements, that the lower end of the cage, designated by the plane LP ends below the upper end of the lower part of the tubular attachment element and thus below the upper end of an inflatable membrane. In this embodiment preferably the axial extension of the lowermost merged strip region that forms the free strip end 2e is more that 50% of the axial height of the cage.

FIG. 6 depict a construction in which the cage C is significantly shorter in axial height AH compared to the other figures. The cage C only surrounds the upper area of the upper tubular part 1e. The axial height AH of the cage C is less than 25% of the axial length of the attachment element 1. The free end strips 2e are essentially straight and essentially parallel to the axis A. More than 51% and accordingly the predominant part of the cage surrounds the tubular attachment element 1. It is essential for this embodiment, that may be combined with any possible construction of the tubular attachment element, that the respective free strip end 2e is formed of a merged strip region 2ms immediately ending after merging. Particularly the length of extension of the free end strip after merging is less than 2 mm, preferably less than 1 mm.

Figure 6A:
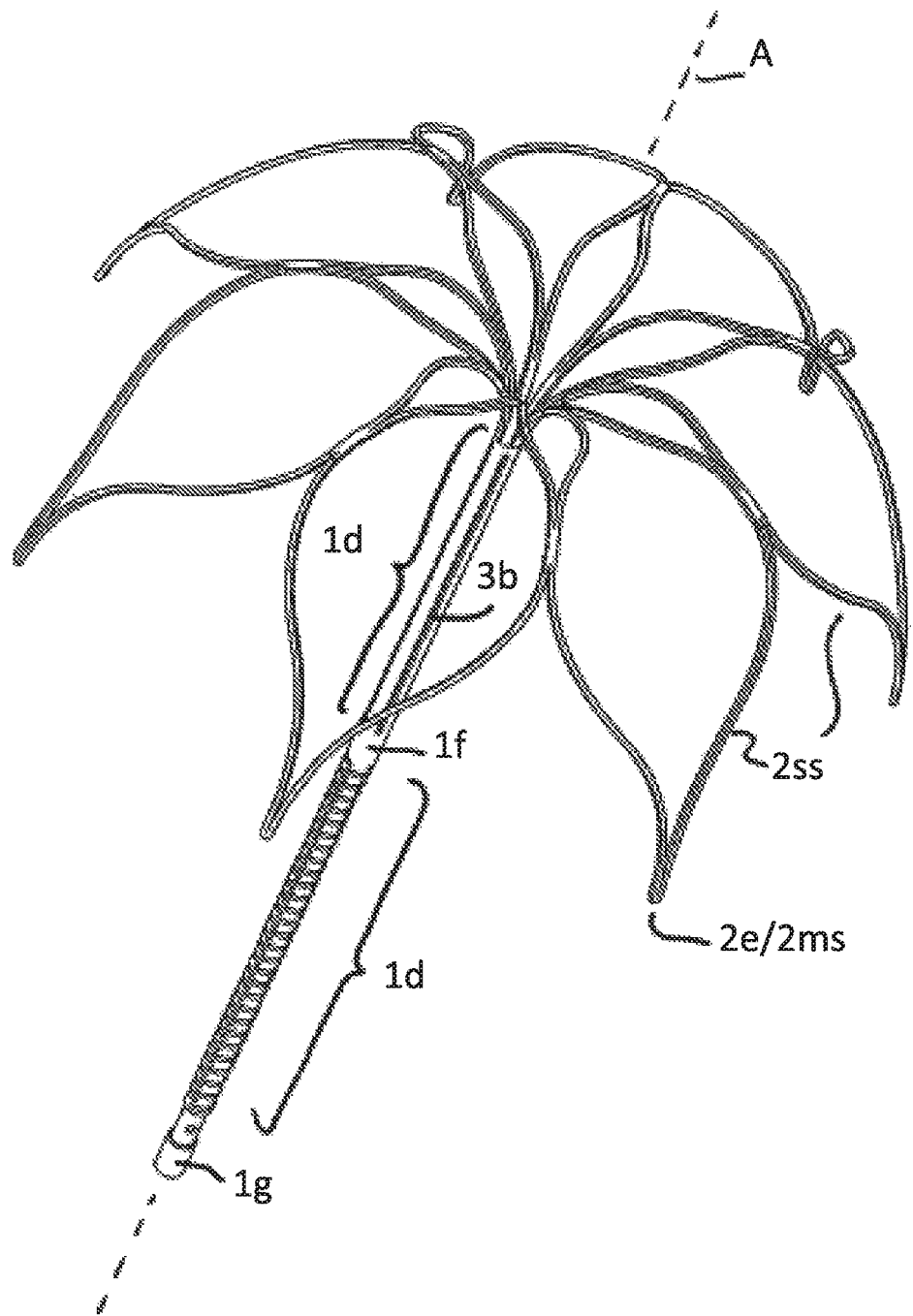
FIG. 6A illustrates a perspective view of a sixth embodiment having the same attachment element as FIGS. 4A-D/ 5A-C but a different anchoring cage
Figure 6B:
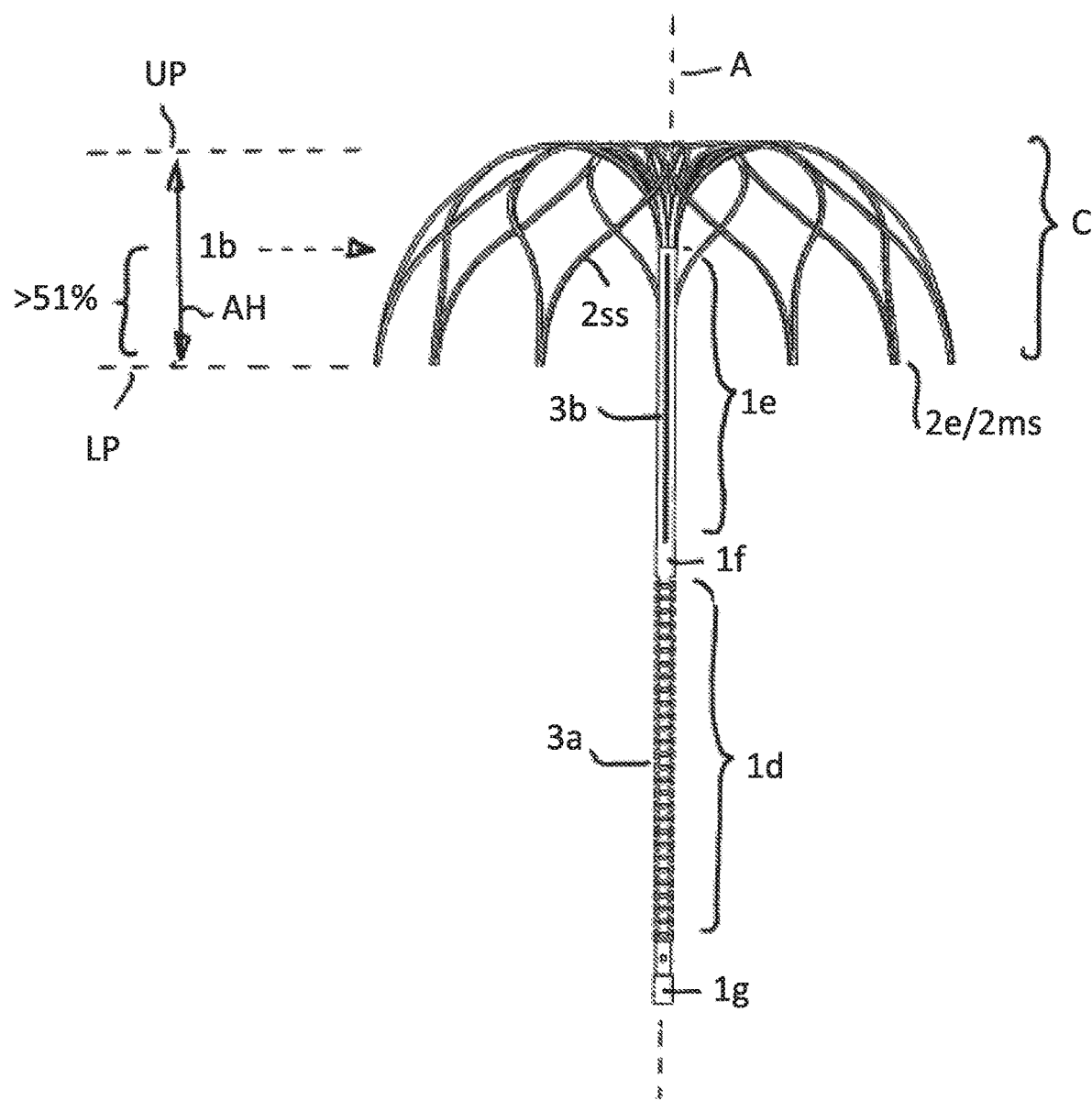
FIG. 6B is a side view of FIG. 6A
Figure 6C:
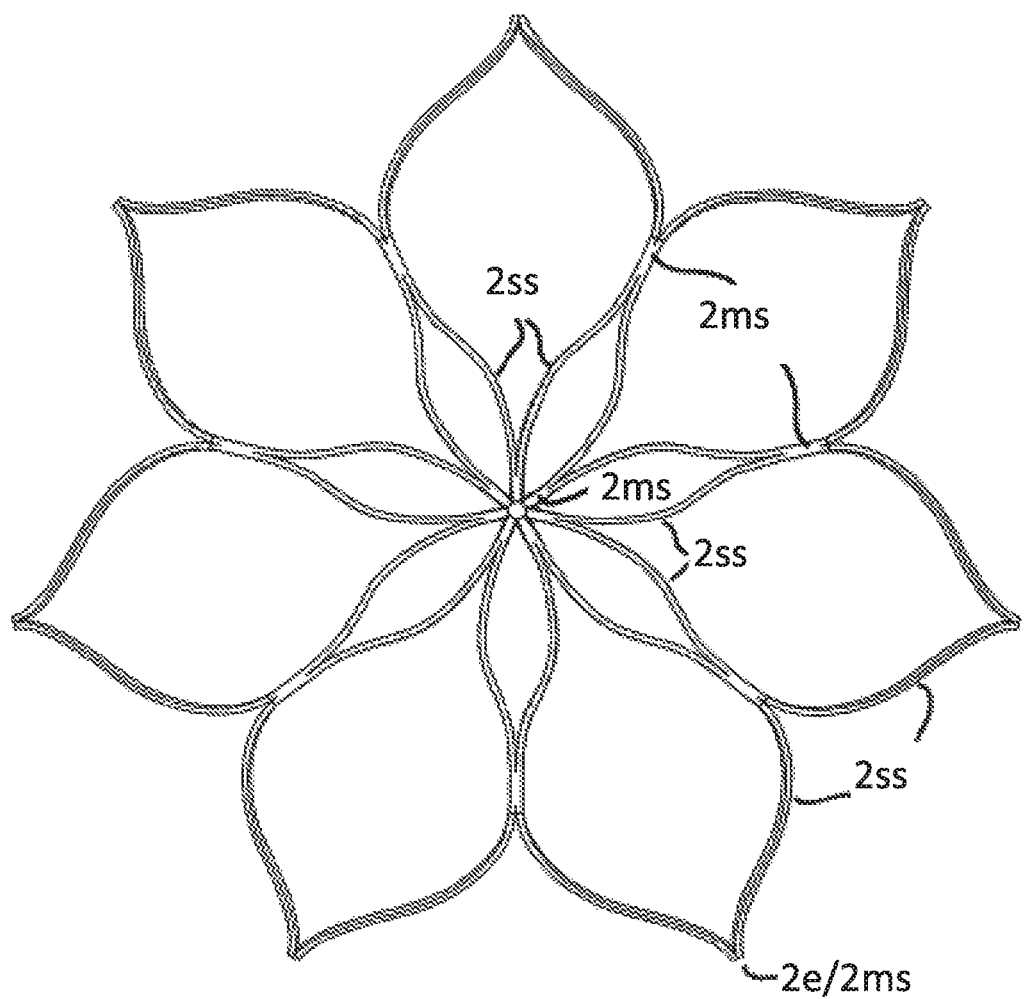
FIG. 6C is a top view of the cage of embodiments according to FIGS. 6A and 6B

FIG. 6A shows the perspective view of this embodiment and FIG. 6B the side view. FIG. 6C shows the top view of the cage C.

It is to be understood in regard to all the shown embodiments, that each respective construction of a tubular attachment element 1 shown in the figures may be combined with each respective cage construction shown in the figures.

FIG. 7A shows a collapsed implant positioned in a catheter 10 having in this particular case an attachment element 1 according to FIG. 5. All other attachment element constructions are also possible. It can be seen that the implant forms a straight device having the free ends 2e of the strips 2 facing towards the implantation site. This site lies in the direction of the arrow 12, that also designates the movement of the implant while pushing through the catheter.

The inflatable membrane IM is folded around the lower tubular part 1d of the attachment element. The free ends have pinholes 7. In this particular case the pull wire is not shown for better visibility of the device.

FIG. 7B shows the situation if the free strip ends 2e are just released from the catheter. By means of internal forces the free strip ends 2e immediately bent over the catheter rim. The free ends 2e may be held together by means of the not shown pull wide fed through the pinholes 7.

Figures 8A, 8B, 8C:
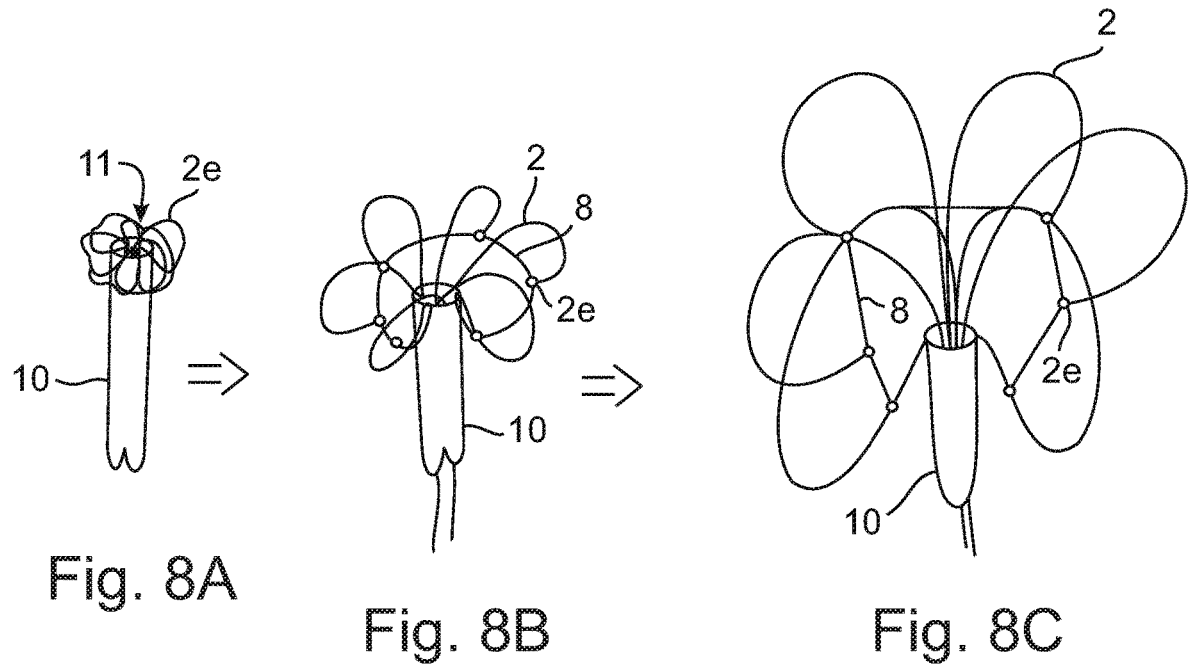

FIG. 8 schematically illustrate the implantation process in different temporal steps. According to FIG. 8A The implant is pushed through a catheter 10 towards the implantation site. The free strip ends 2e are facing the implantation site and according to FIG. 8A are first exiting the catheter opening 11 and immediately bent over the rim of it due to internal forces. FIG. 8A essentially corresponds to FIG. 7B. A pull wire 8 is connecting the free end strips 2e, particularly by feeding the wire through pinholes.

As can be seen in the step of FIG. 8B the pull wire 8 serves to hold the free strip ends 2e close to the catheter 10 thus reducing the self-expansion of the cage. Both ends of the wire 8 are fed thought the catheter 10. Accordingly a surgeon may exert a pulling force to the wire 8. The wire 8 and the free end strips 2e form an annular formation through which the remaining part of the implant is pushed as shown in the steps of FIGS. 8C and 8D.

During the phase of releasing the implant from the catheter 10 the cage is temporarily surrounding the end region of the catheter, particularly during a phase in which the attachment element is still entirely in the catheter 10. The cage will be positioned in front of the catheter opening upon release of an upper part of the tubular attachment element 1.

Figures 8D, 8E:
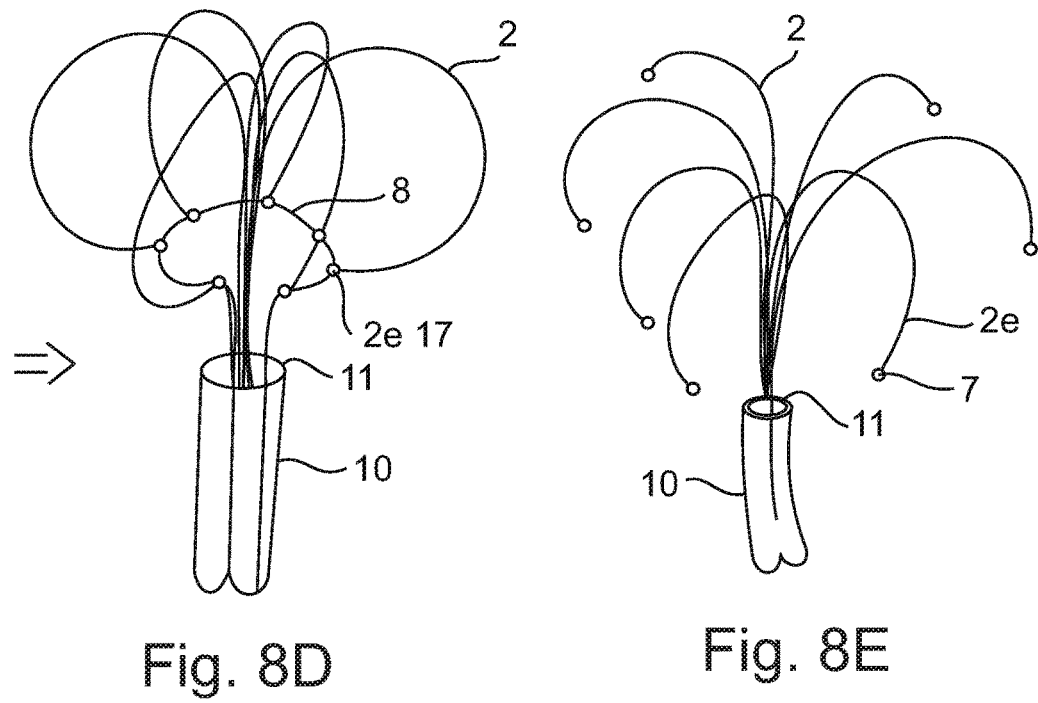

According to the step shown in FIG. 8E the wire 8 is retracted out of the catheter 10 and the cage entirely expands. For reasons of better visibility the interconnections (merging and splitting) of the strips 2 are not shown. Preferably but not shown placing the implant in the intended position within the heart may be performed prior to retracting the wire 8 to assure that the cage only fully expands if it is already correctly placed.

Figure 9:
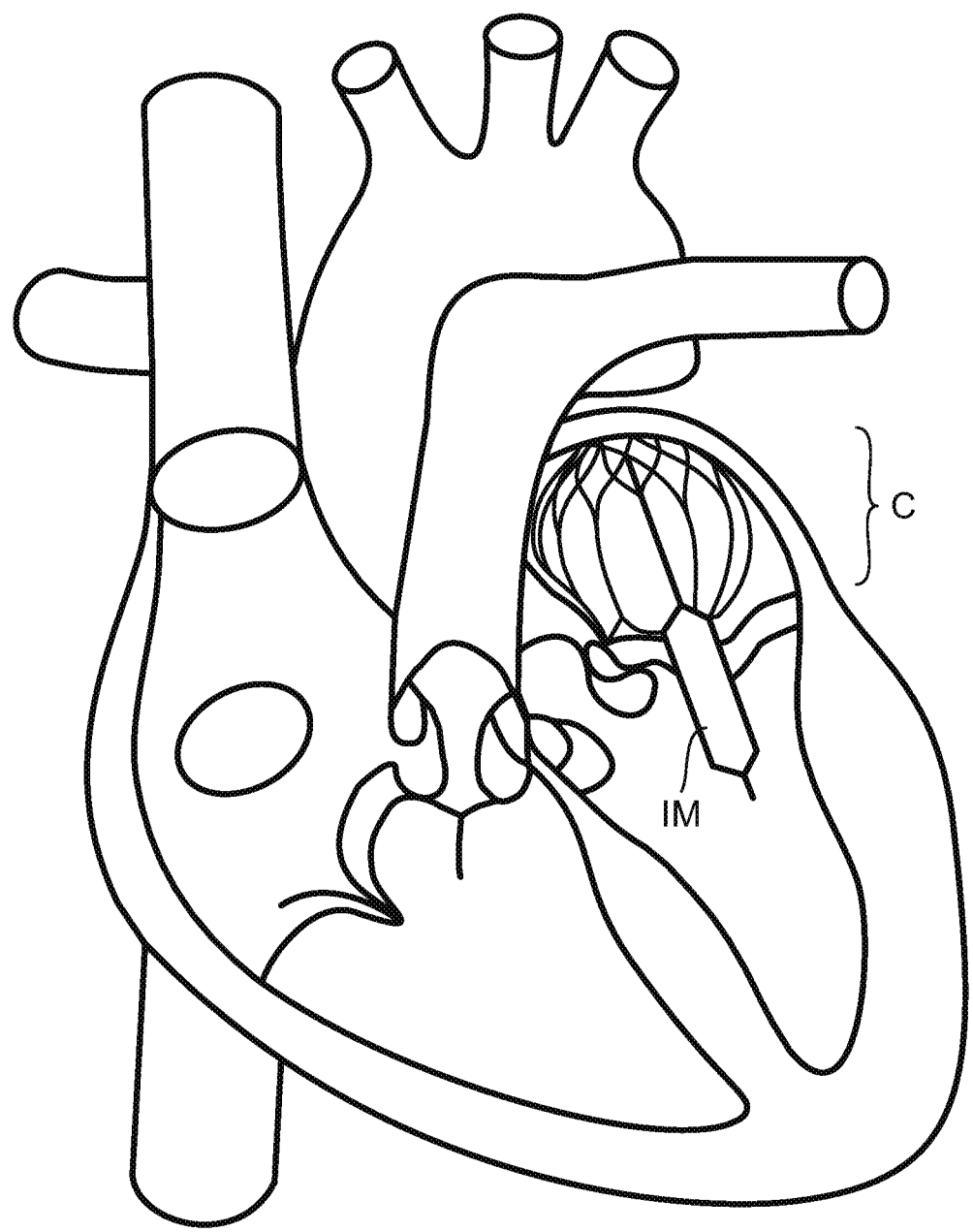
FIG. 9 illustrates the implant according to FIG. 5A-C being correctly positioned in the heart and having the sheath inflated.

FIG. 9 shows the correct position of the implant of FIG. 5 in the native heart. The cage C is positioned in the atrium and the inflatable membrane that surrounds the attachment element is passing through the mitral valve. Accordingly the leaflets of the valve may contact the membrane. Any remaining gap between the leaflets may be closed or at least reduced by the inflated membrane IM.

What is claimed is:

1. Heart implant comprising a tubular attachment element having a lower end and an upper end and a first axially extending lower tubular part being covered by a sheath and a second axially extending upper tubular part being external to the sheath and extending between the first lower tubular part and the upper end of the tubular attachment element, the upper end being split into strips forming an expandable cage being anchorable within the atrium of the heart via surface contact between an exterior surface of the expandable cage and an interior surface of the atrium, wherein in an expanded state, the strips extend from the upper end towards the lower end of the tubular attachment element and form an expanded cage being positioned around at least an upper part of the tubular attachment element, and wherein the lower tubular part and the upper tubular part have the same cross section, and the lower tubular part is coaxially surrounded by an inflatable membrane.

2. Heart implant according to claim 1, wherein at least one of the strips along its extension from the upper end of the tubular attachment element towards the lower end of the tubular attachment element branches into two strips and merges into strip regions.

3. Heart implant according to claim 1, wherein free ends of the strips include a pinhole.

4. Heart implant according to claim 1, wherein in the collapsed state, the cage-forming strips extend away from the upper end of the tubular attachment element in an axial direction pointing from the lower end to the upper end.

5. Heart implant according to claim 1, wherein the tubular attachment element comprises a meshed lateral area, formed from an expanded cut/slotted tube.

6. Heart implant according to claim 5, wherein the meshed lateral area extends at least 90% of the distance between the lower end and the upper end.

7. Heart implant according to claim 5, wherein the meshed lateral area forms an internal scaffold of the sheath directly contacting the scaffold.

8. Heart implant according to claim 1, wherein the lower tubular part has a bigger cross section than the upper tubular part.

9. Heart implant according to claim 1, wherein the lower tubular part comprises a meshed lateral area.

10. Heart implant according to claim 1, wherein the lower tubular part and the upper tubular part include cuts being positioned in a lateral area of each of the lower and upper tubular parts.

11. Heart implant according to claim 10, wherein the lower tubular part and the upper tubular part are axially spaced by a rigid tubular part of the tubular attachment element.

12. Heart implant according to claim 11, wherein the rigid tubular part forms an area of the tubular attachment element to which an upper part of the inflatable membrane is attached.

13. Heart implant according to claim 10, wherein the cuts in the lower tubular part and the cuts in the upper tubular part are arranged in different cut patterns.

14. Heart implant according to claim 13, wherein the cut pattern in the lower tubular part comprises straight cuts extending axially and/or in a circumferential direction.

15. Heart implant according to claim 13, wherein the cut pattern in the upper tubular part comprises at least one straight or helically extending cut.

* * * * *